United States Patent [19]

Depel et al.

[11] Patent Number: 4,610,691
[45] Date of Patent: Sep. 9, 1986

[54] VOICE PROSTHESIS DEVICE

[75] Inventors: William A. Depel, Lowell; Bernd Weinberg; Jerald B. Moon, both of West Lafayette, all of Ind.

[73] Assignees: Purdue Research Foundation, W. Lafayette; Bivona Surgical Instruments, Inc., Gary, both of Ind.

[21] Appl. No.: 509,963

[22] Filed: Jun. 30, 1983

[51] Int. Cl.$^4$ .............................................. A61F 2/20
[52] U.S. Cl. ..................................................... 623/9
[58] Field of Search ........................... 3/1, 3; 272/14; 446/207, 202; 137/855, 856, 895; 156/293, 303.1; 128/203.11; 604/247

[56] References Cited

U.S. PATENT DOCUMENTS

| 155,667 | 10/1874 | Painter | 137/855 |
|---|---|---|---|
| 249,557 | 11/1881 | Trueseale | 137/855 |
| 2,378,613 | 12/1941 | Young et al. | 137/855 |
| 3,628,565 | 12/1971 | McWethy | 137/855 |
| 3,957,046 | 5/1976 | Harris | 128/203.11 |
| 4,137,117 | 1/1979 | Jones | 156/303.1 |
| 4,435,853 | 3/1984 | Blum et al. | 3/1.3 |

Primary Examiner—Richard J. Apley
Assistant Examiner—James Prizant
Attorney, Agent, or Firm—McDougall, Hersh & Scott

[57] ABSTRACT

Voice prosthesis devices of known type to be inserted into a surgical fistula communicating between the trachea and esophagus of a laryngectomized patient have included a one-way valve that permits channeling air from the trachea into the esophagus of the wearer while preventing flow of esophageal material into the trachea. Heretofore, the one-way valves in certain of such prosthesis devices were in the form of a flap-type check valve having a membrane-like flap or disc anchored at a segment of the margin to the interior or intraluminal surface of a tubular housing. The present invention provides an improvement in such voice prosthesis devices in the form of a novel way of anchoring the membrane-like flaps or discs to the tubular housings whereby when the prosthesis devices are manufactured in commercial quantities the method of attachment provides a uniform resistance to airflow for each prosthesis formed of corresponding production components. The pre-determined and uniform resistance to airflow offered by the one-way valves of the present invention is consistently equal to, less than, or greater than the resistance offered by the normal larynx to suit the individual need of the patient.

4 Claims, 13 Drawing Figures

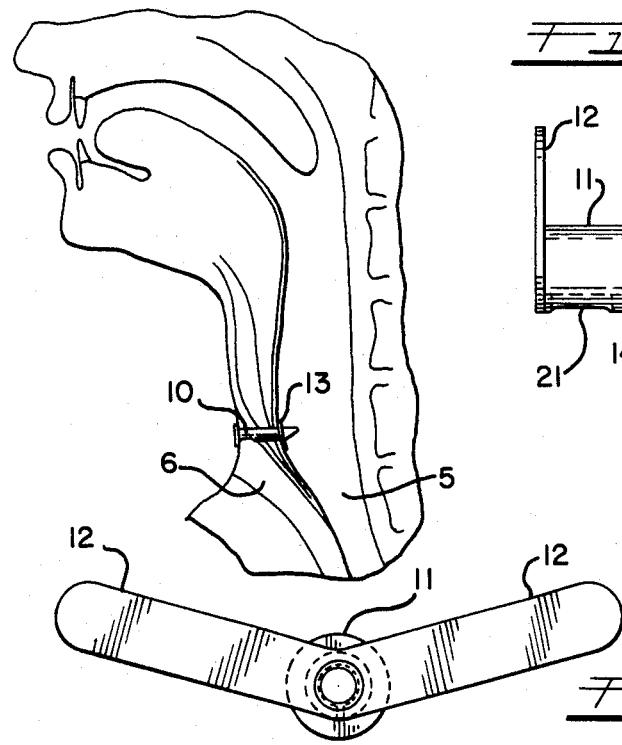
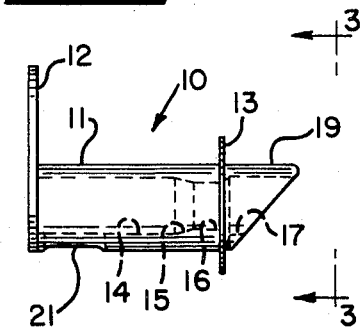
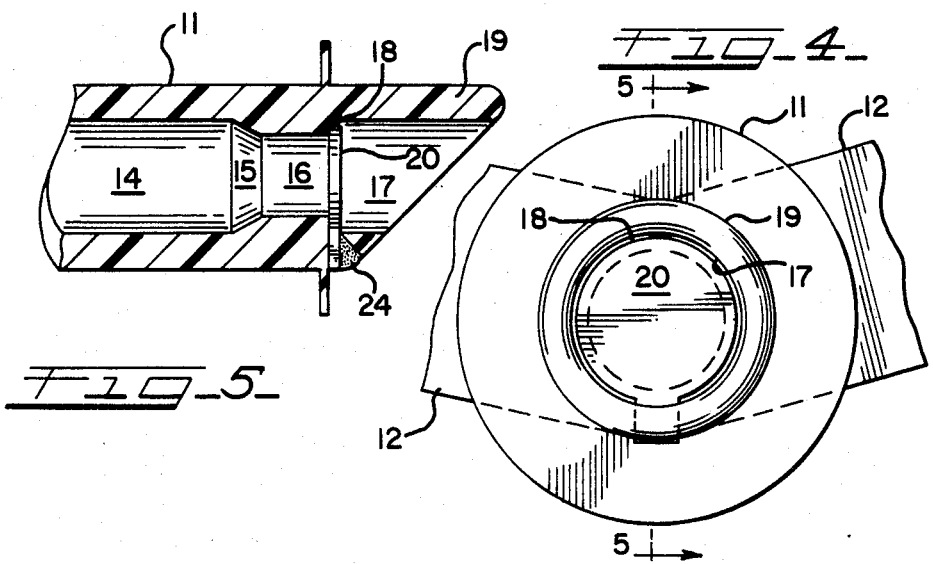

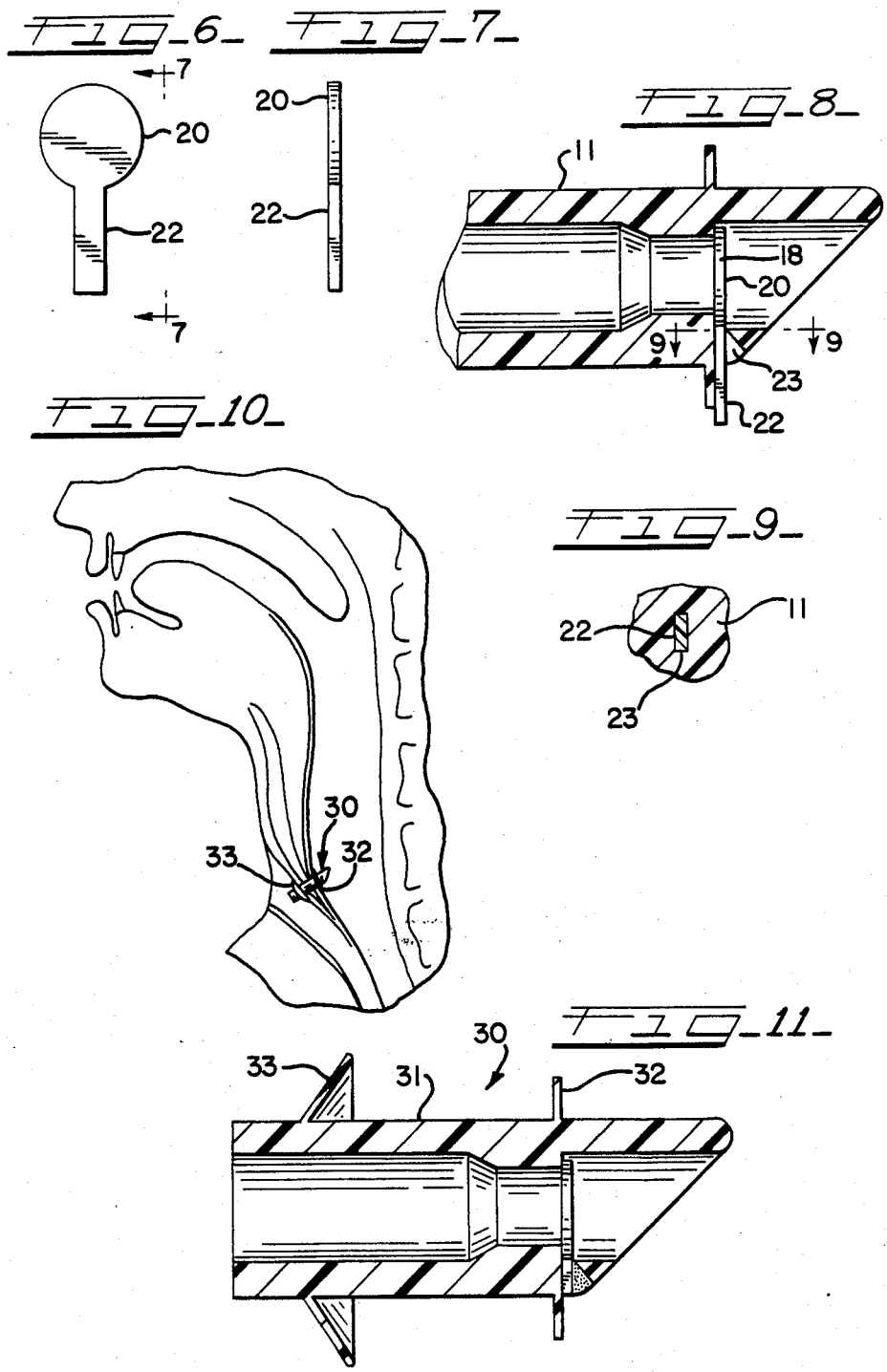

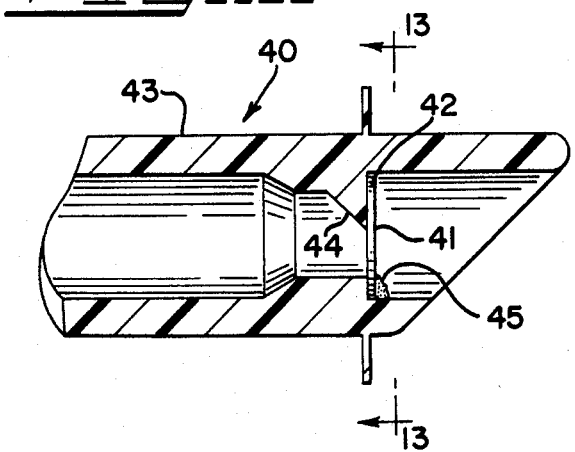
FIG_12_
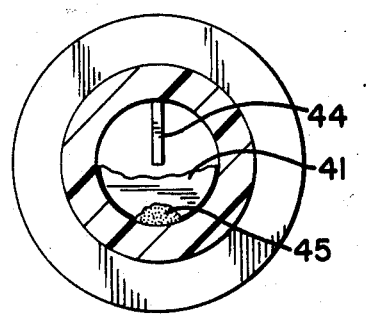
FIG_13_

VOICE PROSTHESIS DEVICE

This invention relates to certain improvements in voice prosthesis devices of the type to be inserted into a surgical fistula communicating between the trachea and esophagus of a laryngectomized patient. The invention relates particularly to the manner in which the membrane-like flap or disc of a flap-type check valve is secured or anchored adjacent its periphery to a housing. The novel way of attaching or anchoring the disc or flap of the check valve is such that a high degree of uniformity of resistance to airflow is obtained when the voice prosthesis devices are manufactured in commercial quantities from corresponding production components.

Voice prosthesis devices of the general type to which the present invention relates are known and have been described in the professional or technical literature, and also in the popular or lay press. (Annals of Otology, Rhinology and Laryngology 91:1982; Newsweek, June 21, 1982, page 70). One known type is the so-called Blom-Singer TM prosthesis and a second is the Panje prosthesis. In both named types, the voice prosthesis is inserted into a surgical fistula that communicates between the trachea and esophagus of a laryngectomized patient.

As originally developed and made available to patients, the Blom-Singer TM voice prosthesis relied on one slit and the Panje voice prosthesis on two intersecting slits in the end of a tubular housing to serve as one-way check valves and allow air to be channeled from the trachea into the esophagus of the wearer. However, such valves offered a resistance to airflow from the trachea to the esophagus in the order of three or more times greater than that offered by the normal larynx. It was found that this often unacceptably high resistance to airflow could be reduced to a value approximating that offered by the normal larynx by the use of one-way flap-type check valves having a membrane-like flap or disc arranged to open and allow air to flow from the trachea to the esophagus and to close and prevent flow of contents of the esophagus in a reverse direction into the trachea. However, it was learned through experience that even when all of the production components of the one-way check valves were substantially identical, upon their assembly in commercial quantities, the manner of attaching or anchoring the membrane-like flaps or discs to the housings resulted in considerable variation in resistance to airflow.

It was discovered in accordance with the present invention, that the membrane-like check valve flaps or discs can be anchored or attached at the peripheries thereof in a novel manner which results in a high degree of uniformity to airflow resistance when production components are assembled in commercial quantities.

The object of the invention, generally stated, is the provision in production quantities of voice prosthesis devices of the type to be worn by laryngectomized patients in a fistula communicating between the trachea and the esophagus, characterized by uniform resistance to airflow approximating that offered by the normal larynx.

More particularly, the object of the invention is the provision of essentially uniform and desirably low airflow resistance in commercially produced voice prosthesis devices of the type to be worn in a fistula communicating between the trachea and the esophagus of the wearer and including a housing having an air inlet port opening into the trachea and an outlet port opening into the esophagus, and a one-way check valve positioned between the inlet and outlet ports and including a valve seat within the housing and a membrane-like flap or disc anchored adjacent its periphery to the housing so as to close against the valve seat and prevent flow of esophageal contents flowing from the esophagus into the trachea.

Otherwise stated, the object of the invention is the provision of an improved manner and technique of anchoring or securing the membrane-like flaps or discs of the valves in the above type of voice prosthesis devices in such manner that when assembled or produced on a commercial scale from standardized production components, the resistance to airflow will be substantially uniform and equal to, less than or greater than the resistance to airflow offered by the normal larynx, depending upon the modulus and hardness of the membrane-like flap or disc member and the particular type of material from which it is formed.

Still another object of the invention is an improved method of making voice prosthesis devices of the foregoing type.

By selecting a particular modulus and hardness for the membrane-like flaps or discs of the one-way check valves used in the voice prosthesis devices of this invention, and by attaching or anchoring the same adjacent the periphery of each flap or disc to the prosthesis housing according to the invention, the voice prosthesis devices can be readily produced in commercial quantities with a pre-determined uniform resistance to airflow which may be equal to, less than or greater than the resistance offered by the normal larynx, so as to suit the individual needs of various patients.

For a more complete understanding of the nature and scope of the invention, reference may now be had to the following detailed description of two presently preferred embodiments thereof as shown in the accompanying drawings wherein:

FIG. 1 is a diagrammatic view showing a voice prosthesis device forming one embodiment of the invention inserted in a fistula communicating between the trachea and the esophagus of a laryngectomized patient.

FIG. 2 is a side elevational view on enlarged scale of the voice prosthesis device shown in FIG. 1.

FIG. 3 is an end elevational view taken on line 3—3 of FIG. 2.

FIG. 4 is a fragmentary end elevational view corresponding to FIG. 3 on a substantially enlarged scale.

FIG. 5 is a fragmentary longitudinal sectional view taken on line 5—5 of FIG. 4.

FIG. 6 is an elevational view of a membrane-like flap or disc valve member forming a component of the voice prosthesis device shown in FIGS. 1-5.

FIG. 7 is an edge elevational view of the flap or disc taken on line 7—7 of FIG. 6.

FIG. 8 is a longitudinal sectional view corresponding to FIG. 5 showing the membrane-like flap or disc valve member of FIGS. 6 and 7 in place in the tubular housing before the flap or disc is cemented in place in the assembly operation.

FIG. 9 is a fragmentary detail sectional view taken on line 9—9 of FIG. 8.

FIG. 10 is a diagrammatic view similar to FIG. 1 and showing a second embodiment of the invention inserted in the fistula provided therefor in a laryngectomized patient.

FIG. 11 is a longitudinal sectional view on enlarged scale through the prosthesis device shown in FIG. 10.

FIG. 12 is a fragmentary longitudinal sectional view similar to FIG. 5 but showing the known manner in which the membrane-like flap or disc valve member was anchored or secured in place in the housing prior to the present invention.

FIG. 13 is a sectional view taken on line 13—13 of FIG. 12 with the upper portion of the valve flap or disc being broken away.

Referring to FIG. 1, the esophagus of the patient is indicated at 5 and the trachea at 6. The patient is provided with a surgical fistula communicating between the trachea 6 and the esophagus 5 for reception of a voice prosthesis device designated at 10. This particular prosthesis device corresponds generally to one of two known types, namely, the so-called Blom-Singer TM prosthesis. The device 10 has a tubular body or housing 11 which may be injection molded in known manner from a medical grade silicone material of known type.

The outer end of the device 10 is exposed and retained in position by a pair of laterally-extending, skin-adhering tabs 12—12. Adjacent its inner end, the tubular housing or body 11 is provided with an integral retaining flange 13 which engages the front wall of the esophagus as shown in FIG. 1.

Referring particularly to FIGS. 2, 5 and 8, it will be seen that the bore extending through the tubular housing 11 has four different sections designated at 14, 15, 16 and 17. The bore section 14 is the longest and extends from the outer end of the device inwardly to the frusto-conical transition section 15 which joins section 14 to the shorter and smaller diameter section 16. The inner end of the section 16 joins the bore section 17 adjacent the inner end of the device at a circumferential radial shoulder 18 (FIGS. 5 and 8). This shoulder serves as a valve seat for a membrane-like flap or disc 20 which forms the moving part of a one-way check valve. The flap or disc 20 is flexible and formed of a water-resistant material such as silicone rubber or similar materials.

While the tubular body or housing 11 and the valve flap or disc 20 are circular in cross-section and shape, respectively, it will be understood that they may be oval in cross-section and shape.

The tubular body 11 has an elongated air inlet port 21 in the underside which provides communication between the trachea 6 and the bore 14. It will be seen that the outer end of the bore section 17 constitutes an air outlet port which opens into the esophagus. The one-way check valve provided by the membrane-like flap or disc 20 and the valve seat 18 serves to allow air to be channeled from the trachea 6 into the esophagus 5 during speaking, and, at other times, to close off communication between the esophagus and the trachea so as to prevent flow of esophageal contents (whether gaseous, liquid or solid) from the esophagus into the trachea.

The inner end of the tubular housing 11 is slanted, preferably at an angle of approximately 45°, so as to facilitate insertion of the device 10 into the fistula provided therefor and to also provide an overhang or hood 19 that shields the bore section 17 from material passing downwardly through the esophagus 5.

The present invention is particularly concerned with the technique and manner in which the membrane-like valve flap or disc 20 is anchored or secured in place in the housing 11. Referring to FIGS. 6-9, it will be noted that the circular valve flap or disc 20 has a tab-like extension or projection 22 extending integrally therefrom. The housing or body 11 is provided with an outwardly diverging aperture 23 (FIGS. 8 and 9) for receiving the tab or projection 22. The aperture 23 is most restricted at its inner or upper end whereat it has approximately the same dimensions as the cross-section of the tab 22, while allowing the tab 22 to be readily inserted downwardly therethrough.

After the valve flap 20 has been fully inserted into the body 11 with its integral projection 22 extending downwardly through the aperture 23, a drop of moisture-resistant cement 24 (FIG. 5) is deposited into the pocket or recess provided by the aperture 23, thereby securing and anchoring the projection 22 firmly in place and sealing off the aperture 23. After the cement 24 has solidified, the projecting end portion of the projection 22 is severed leaving the finished assembly as shown in FIG. 5.

It will be seen from FIG. 5 that the membrane-like valve flap or disc 20 is normally seated against the valve seat 18. However, when there is sufficient differential in pressure on opposite sides of the flap or disc 20, as created in the wearer's act in speaking and producing a flow of air from the trachea 6 toward the esophagus 5, the flap or disc 20 will pivot or hinge at the integral connection or juncture between the projection 22 and the periphery of the flap or disc 20, thereby coming unseated and allowing air to flow through the prosthesis device 10 and enter the esophagus 5 for speaking.

The tubular housing or body 11 and the valve flap or disc 20 can be produced on a production basis so as to meet appropriate specifications and tolerances. In other words, the exemplars of the bodies or housings 11 and the valve members 20 produced on a quantity production basis will be substantially identical for all practical purposes.

It will be appreciated that the assembly of the membrane-like flaps or discs 20 into the valve housings or bodies 11 is such that the resulting assemblies will be essentially identical. Furthermore, since the hinging or pivoting action of the circular flaps or discs 20 occurs at substantially identical locations and cross-sectional areas that are essentially identical from assembly to assembly, the resistance to airflow offered by the one-way check valves, and, in turn, the prosthesis devices 10 will be essentially uniform from exemplar to exemplar.

The actual resistance to airflow offered by the one-way check valve in any of the voice prosthesis devices 10 made in accordance with this invention will depend on two factors. One is the area and shape of the integral connection between the circular, oval (or otherwise shaped) valve flap or disc 20 and its projection 22. The other factor is the nature of the particular material from which the valve flap or disc 20 is formed.

In practice, it has been found that most laryngectomized patients are best served with a voice prosthesis device 10 having a resistance to airflow which is approximately the same as that offered by a normal larynx. However, certain patients will need or prefer an airflow resistance somewhat lower and others an airflow resistance somewhat higher than that offered by the normal larynx. In production, these differences in uniform resistance to airflow can readily be obtained by variations in the modulus and hardness of the material from which the valve flaps or discs 20 and projections 22 are formed. Thus, increased modulus and hardness result in decreases in resistance to airflow.

The present invention, as incorporated in the voice prosthesis devices 10 of FIGS. 1-9, may also be incorporated in the above-mentioned Panje implant-style of voice prosthesis. Such a second embodiment of the invention is shown in FIGS. 10 and 11 wherein the voice prosthesis device is designated generally at 30. The housing or body 31 of the device 30 is somewhat shorter than the body or housing 11 of the device 10, due to the fact that the device 30 needs only to span the surgical fistula between adjacent walls of the trachea and esophagus of the wearer with slight projections on opposite ends. While the inner end of the device 30, which resides in the esophagus, is provided with a retention flange 32 corresponding to the retention flange 13 of the prosthesis device 10, it is also provided with a frusto-conical shaped retention flange 33 instead of the retention flaps 12—12 of the device 10. The flange 33 is preferably in the form of a Bellville washer for yielding engagement against the adjacent surface of the trachea. Except for the foregoing differences, the voice prosthesis device 30 of the Panje type corresponds to the device 10 of FIGS. 1–9. Furthermore, in respect to the present invention, the voice prosthesis device 30, of FIGS. 10 and 11, is identical with that of the voice prosthesis device 10 of FIGS. 1–9.

Prior to the present invention, the membrane-like flaps or discs of the one-way check valves in voice prosthesis devices of the tubular type represented by devices 10 have been secured in place in the manner shown in the voice prosthesis device 40 in FIGS. 12 and 13. Referring to FIGS. 12 and 13, a voice prosthesis device is indicated at 40 wherein a membrane-like flap or disc 41 seats against a circumferential shoulder or valve seat 42. The bore of the tubular body 43 is provided with an inwardly extending radial projection 44 which acts to prevent the valve flap or disc 41 from becoming accidentally unseated in the wrong direction.

As shown in FIGS. 12 and 13, the flap or disc 41 of the one-way check valve is anchored or attached to the valve body 43 by a deposit of cement 45 in accordance with known manner. In production, it is difficult to have each deposit of cement 45 essentially identical in placement, amount, size and shape. Accordingly, there will be appreciable difference from assembly to assembly in respect to the location, size and shape of the arcuate cross-sectional area about which the valve flap or disc 41 hinges or pivots. Consequently, there will be an appreciable variation in the resistance to airflow offered by the voice prosthesis devices 40 when produced in production quantities. As explained above, the manner of attachment of the membrane-like flaps or discs of the one-way check valves provided by the present invention eliminates such variations and differences in resistance to airflow.

It will be understood certain changes and modifications can be made in the voice prosthesis devices 10 and 30 in addition to those mentioned or suggested, and that other embodiments may be made, without departing from the spirit and scope of the invention set forth in the following claims.

We claim:

1. In a voice prosthesis device to be worn in a fistula communicating between the trachea and esophagus of the wearer and including a housing having an air inlet port opening into the trachea and having an air outlet port opening into the esophagus, and a one-way check valve including a valve seat within said housing and a membrane-like disc anchored adjacent its periphery to said housing so as to close against said valve seat and prevent flow of esophageal contents from the esophagus into the trachea, the improvement, comprising:

said disc including one-piece attachment means which is smaller than the disc and extends outwardly beyond the periphery of said disc and aperture means dimensioned to receive the attachment means whereby the disc is effectively hinged primarily through the attachment means at a point spaced from the periphery of the disc so that the disc remains substantially flat in response to the opening of the disc by pivotally moving away from said valve seat.

2. The improvement called for in claim 1 wherein said housing is tubular and said attachment means includes a projection extending through a flap-receiving aperture in said housing, said projection being secured in said aperture.

3. The improvement called for in claim 2 wherein said flap-receiving aperture widens outwardly so as to provide a cement-receiving pocket.

4. The improvement called for in claim 2 wherein the resistance to airflow offered by said one-way check valve is proportional to the cross-sectional area whereat said integral projection integrally connects with said flap or disc.

* * * * *